US009867739B2

(12) United States Patent
Gross et al.

(10) Patent No.: US 9,867,739 B2
(45) Date of Patent: Jan. 16, 2018

(54) ABSORBENT ARTICLE HAVING A CLEFTED TOPSHEET

(71) Applicant: The Procter & Gamble Company, Cincinnati, OH (US)

(72) Inventors: Sarah Beth Gross, Harrison, OH (US); Richard George Coe, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 639 days.

(21) Appl. No.: 14/135,755

(22) Filed: Dec. 20, 2013

(65) Prior Publication Data

US 2015/0173970 A1 Jun. 25, 2015

(51) Int. Cl.
| A61F 13/15 | (2006.01) |
| A61F 13/47 | (2006.01) |
| A61F 13/513 | (2006.01) |
| B29C 59/04 | (2006.01) |
| A61F 13/476 | (2006.01) |
| A61F 13/45 | (2006.01) |
| A61F 13/51 | (2006.01) |
| A61F 13/511 | (2006.01) |
| A61F 13/512 | (2006.01) |

(52) U.S. Cl.
CPC .... *A61F 13/4704* (2013.01); *A61F 13/15731* (2013.01); *A61F 13/476* (2013.01); *A61F 13/512* (2013.01); *A61F 13/513* (2013.01); *A61F 13/5116* (2013.01); *A61F 13/51121* (2013.01); *B29C 59/046* (2013.01); *A61F 13/47* (2013.01); *A61F 13/5123* (2013.01); *A61F 13/5126* (2013.01); *A61F 13/51104* (2013.01); *A61F 2013/15975* (2013.01); *A61F 2013/4587* (2013.01); *A61F 2013/5128* (2013.01); *A61F 2013/51088* (2013.01)

(58) Field of Classification Search
CPC .................. A61F 13/47; A61F 13/4704; A61F 13/14731; A61F 13/15957; A61F 13/513; A61F 13/512; A61F 13/5123; A61F 13/5126; A61F 2013/4587; A61F 2013/15957; A61F 2013/51008; A61F 2013/5128
See application file for complete search history.

(56) References Cited

U.S. PATENT DOCUMENTS

| 5,518,801 | A | 5/1996 | Chappell et al. |
| 7,252,656 | B2 | 8/2007 | Bonelli et al. |
| 7,410,683 | B2 | 8/2008 | Curro et al. |
| 7,648,752 | B2 | 1/2010 | Hoying et al. |
| 7,967,801 | B2 | 6/2011 | Hammons et al. |
| 7,993,317 | B2 | 8/2011 | Hammons et al. |

(Continued)

*Primary Examiner* — Jacqueline Stephens
(74) *Attorney, Agent, or Firm* — Brian M. Bolam; Dara M. Kendall; Andrew J. Hagerty

(57) ABSTRACT

An absorbent article comprising a topsheet and laterally extending wings is disclosed. The topsheet having a plurality of clefts is disclosed. The plurality of clefts of the first type can be formed by urging discrete portions of the topsheet in a first direction and the plurality of clefts of the second type are formed by urging discrete portions of the topsheet in a second direction that is different than the first direction. The first or second plurality of clefts can be positioned proximate to a wing or flap of the absorbent article.

20 Claims, 10 Drawing Sheets

(56) References Cited

U.S. PATENT DOCUMENTS

| | | |
|---|---|---|
| 8,058,501 B2 | 11/2011 | Hammons et al. |
| 2005/0064136 A1 | 3/2005 | Turner et al. |
| 2010/0035014 A1 | 2/2010 | Hammons et al. |
| 2010/0036346 A1* | 2/2010 | Hammons ............. A61F 13/512 604/378 |
| 2012/0064280 A1 | 3/2012 | Hammons et al. |

* cited by examiner

ABSORBENT ARTICLE HAVING A CLEFTED TOPSHEET

FIELD

The present disclosure relates to disposable absorbent articles with wings or side flaps comprising topsheet materials that have a variety of structurally modified zones, including zones that comprise clefts. The present invention also relates to methods for texturing webs, particularly those useful as topsheets for absorbent articles.

BACKGROUND

Disposable absorbent articles with wings refer herein to personal care articles for absorbing bodily discharges. Typically, the articles having wings include catamenial napkins for absorbing menses (as well as other vaginal exudates), pantiliners, adult incontinence pads for absorbing urine, and the like. These wings have been used to provide certain functions including integrating the article with the panties of a wearer for proper positioning of the article proximate the body of the wearer and preventing panties from "staining" when the article fails to prevent leakage. In use, absorbent articles are stressed by a variety of fluid handling demands. For instance, the central portion of the pad may be assaulted with fluid flow that may either be a trickle or a gush of fluid. If the wearer is lying down on her front or back, fluid may have a tendency to run off of the front end or rear end of the absorbent article. Typical absorbent articles are approximately the same width as the crotch of the wearer's undergarment, which can be somewhat narrow. Thus, there is potential for fluid to run off the sides of the absorbent article and soil the wings of the absorbent article, if present, or soil the wearer's undergarment and/or clothing.

Wings can be formed, at least partially, from a polymer film. Polymer films generally lack absorbency and often have a plastic-like texture and/or a shiny appearance. Based on the texture and appearance of the film, a consumer may deem the wings to be of lower quality or otherwise lack a desired level of fluid management or comfort. Given the variety of fluid handling demands placed on different portions of an absorbent article, the desire to improve the texture, comfort, appearance, and function of wings of an absorbent article, there is continuing and unaddressed need for absorbent articles having a topsheet that has different regions arranged to provide fluid handling benefits where needed and provide other functional, aesthetic, and/or performance benefits where needed.

SUMMARY

In accordance with one embodiment, there has now been provided an absorbent article comprising a topsheet, a backsheet opposing the topsheet, and an absorbent core disposed between the topsheet and the backsheet. The topsheet comprises a polymeric film, a longitudinal centerline, and a transverse centerline perpendicular thereto. One or more wings extend along a respective axis parallel to the transverse centerline. Each wing defines a first portion of the topsheet and a second portion of the topsheet. The topsheet comprises a third portion and a fourth portion that are on opposing sides of the longitudinal centerline and that are each positioned intermediate the first and second portions along an axis parallel to the transverse centerline. Each portion includes a respective structurally modified zone. The first and second structurally modified zones comprise a plurality of clefts that are formed by urging discrete portions of the polymeric film in a direction towards the backsheet. The third and fourth structurally modified zones comprise a plurality of film ruptures that are formed by urging discrete portions of the polymeric film in a direction that is away from the backsheet.

In accordance with a second embodiment, there has now been provided an absorbent article comprising a main body including an absorbent core, a longitudinal centerline and a transverse centerline. First and second wings extend in a direction parallel to the transverse centerline and outwardly from the main body on opposing sides of the longitudinal centerline. A topsheet comprising a polymeric film extends across the first wing, the main body, and the second wing, such that the topsheet comprises a first wing portion, a second wing portion and a main body portion. A backsheet extends across the first wing, the main body, and the second wing. The first and second wing portions of the topsheet comprise a plurality of clefts that comprise cleft sidewalls that extend in a direction towards the backsheet and/or partially contact the backsheet.

In accordance with another embodiment, there has now been provided an absorbent article comprising a main body including an absorbent core, a longitudinal centerline and a transverse centerline. First and second wings extend in a direction parallel to the transverse centerline and outwardly from the main body on opposing sides of the longitudinal centerline. A topsheet comprising a polymeric film extends across the first wing, the main body, and the second wing, such that the topsheet comprises a first wing portion, a second wing portion and a main body portion. A backsheet extends across the first wing, the main body, and the second wing. The first and second wing portions of the topsheet comprise a plurality of apertures that comprise aperture sidewalls that extend in a first direction. And the first and second wing portions of the topsheet comprise a plurality of clefts that comprise cleft sidewalls that extend in a second direction that is different from the first direction.

In accordance with another embodiment, there has now been provided an absorbent article comprising a main body having a longitudinal centerline and a transverse centerline and an absorbent core. First and second wings extend in directions parallel to the transverse centerline and outwardly from the main body on opposing sides of the longitudinal centerline. A topsheet comprising a first wing portion, a second wing portion, and a main body portion disposed between the first and second wing portions. The topsheet comprises only a polymeric film that extends across the first wing and the second wing, and comprises both a polymeric film and nonwoven in the main body portion. The first and second wing portions of the topsheet comprise a plurality of clefts having cleft sidewalls extending from the polymeric film. And the main body portion of the topsheet comprises a plurality of polymeric film ruptures with fiber tufts originating from the nonwoven extending therethrough.

In accordance with yet another embodiment, there has now been provided a method for texturing a web of material, the method comprises a step (a) of providing a laminate web of material that includes a polymer film and a nonwoven layer. The polymer film extends beyond the periphery of the nonwoven layer to define a first area that only includes the polymer film and a second area that includes both the polymer film and the nonwoven layer. The polymer film comprises a first surface and an opposing second surface that faces the nonwoven layer. The method comprises a step (b) of impacting the first surface in the first area to create a plurality of polymer film clefts. And the method comprises a step (c) of impacting the second surface in the second area to create a plurality of polymer film ruptures and fiber tufts extending into and/or through the same.

In accordance with another embodiment, there has now been provided an apparatus for texturing a web of material. The apparatus comprises a first roll and a second roll that intermesh along an interfacing width. The first roll includes a first plurality of teeth that are disposed about the circumference of the first roll and that are positioned at a first location along the interfacing width. The first roll further includes a first valley that is positioned at a second location along the interfacing width. The second roll includes a second plurality of teeth that are disposed about the circumference of the second roll and that are positioned at the second location along the interfacing width. These second plurality of teeth engage the first valley. The second roll further includes a second valley that is positioned at the first location along the interfacing width and that engages the first plurality of teeth.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein.

DETAILED DESCRIPTION

Figure 1:
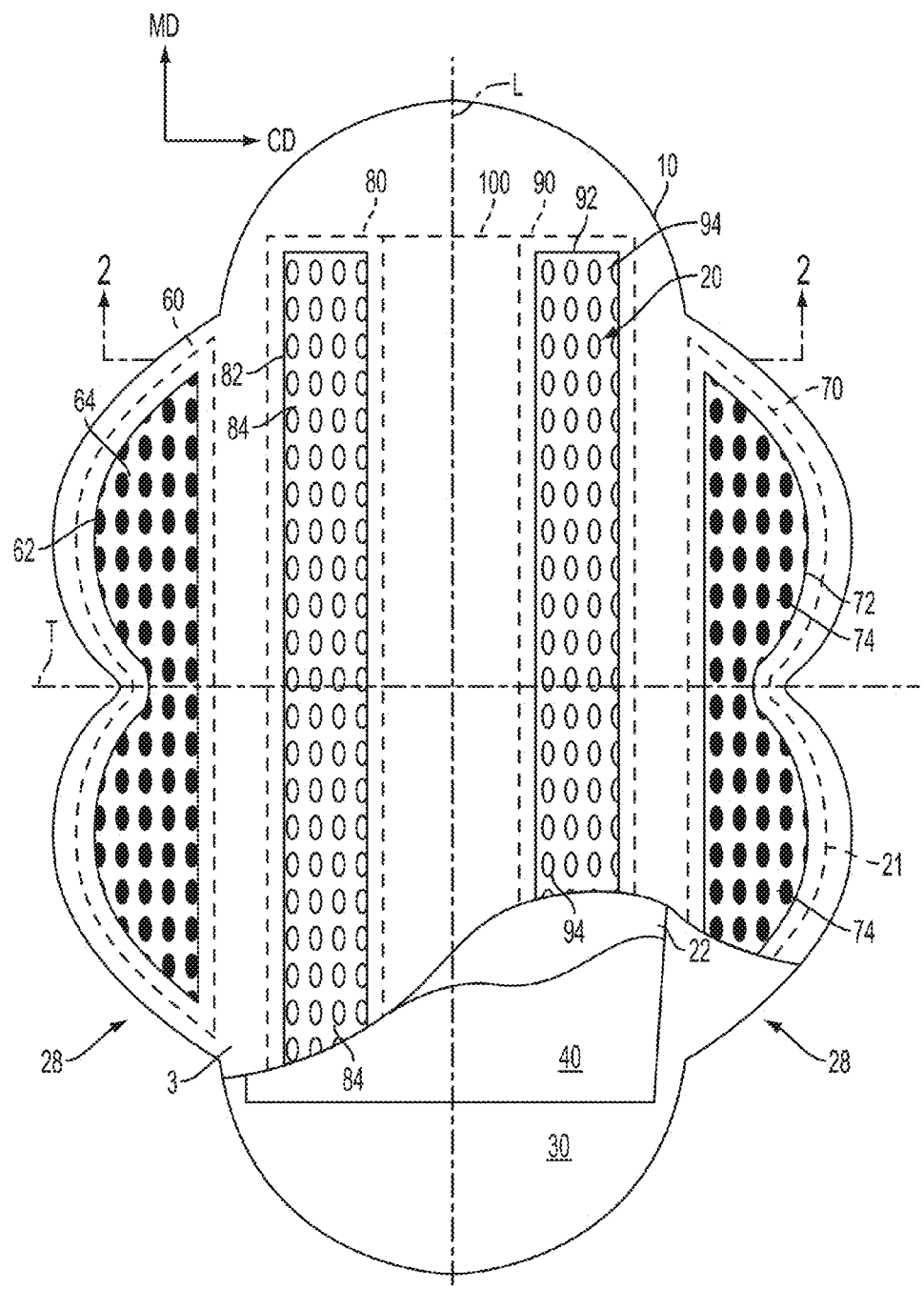
FIG. 1 is a plan view of an embodiment of an absorbent article 10 having a topsheet with different structurally modified regions.

Various non-limiting embodiments of the present disclosure will now be described to provide an overall understanding of absorbent articles that having clefted topsheets providing multiple textures. One or more examples of these non-limiting embodiments are illustrated in the accompanying drawings. Those of ordinary skill in the art will understand that the topsheets and absorbent articles described herein and illustrated in the accompanying drawings are non-limiting embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

As used herein, "absorbent article" refers to disposable devices such as infant, child, or adult diapers, pant-style diapers, training pants, sanitary napkins, diaper inserts, and the like which are placed against or in proximity to the body of the wearer to absorb and contain the various exudates discharged from the body. Typically, these articles comprise a topsheet, backsheet, an absorbent core, and typically other components, with the absorbent core normally placed at least partially between the backsheet and the topsheet. The absorbent articles of the present disclosure will be further illustrated in the below description and in the Figures in the form of a sanitary napkin. Nothing in this description should be, however, considered limiting the scope of the claims. As such the present disclosure applies to any suitable form of absorbent articles (e.g., training pants, adult incontinence products, diapers, and so forth).

As used herein, "absorbent core" refers to a structure typically disposed between a topsheet and backsheet of an absorbent article for absorbing and containing liquid received by the absorbent article. The absorbent core can comprise one or more substrate layers, an absorbent material disposed on the one or more substrate layers, and a thermoplastic adhesive composition on the absorbent material. The thermoplastic adhesive composition can be on the absorbent material and at least a portion of the one or more substrate layers. The absorbent core does not include an acquisition system, a topsheet, or a backsheet of the absorbent article.

As used herein, "area density" refers to the number of features per unit area. The features can be macro features or micro features, as described herein.

"Cleft" includes an aperture, a rupture, a slit, an indentation, a dimple, an embossment, and the like, wherein the previously mentioned structure comprises sidewalls that are partially collapsed, buckled, folded, or tucked. Clefts are structural modifications that are created in a single layer of material, and do not include modifications resulting from impacting one layer of a multilayer web with an adjacent layer wherein the two adjacent layers are both deformed from the impacting force.

As used herein, the term "machine direction" or "MD" means the path that material, such as a web, follows through a manufacturing process.

As used herein, the term "cross-machine direction" or "CD" means the path that is perpendicular to the machine direction in the plane of the web.

As used herein, "nonwoven web" refers to a manufactured sheet, web, or batt of directionally or randomly orientated fibers. The fibers can be of natural or man-made origin and can be staple or continuous filaments or be formed in situ. Commercially available fibers can have diameters ranging from less than about 1 microns to more than about 200 microns and can come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding, wetlaying and airlaying. The basis weight of nonwoven webs is usually expressed in grams per square meter (g/m2 or gsm).

As used herein, the term "polymer" is used in its conventional meaning, and generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries. In general, any of the known polymer types can be used, for example, polyolefinic polymers such as polypropylene or polyethylene can be used either as monocomponent fibers or bicomponent fibers. Other polymers such as PVA, PET polyesters, metallocene catalyst elastomers, nylon and blends thereof can be used. Any or all of the polymers can be cross-linked if desired.

As used herein, "structurally modified", with respect to constituent materials, means that the constituent material (or materials) is altered such that a material that is structurally modified differs in mechanical, performance, and/or sensorial behavior as compared to the unmodified material. For instance, the structurally modified material can transmit stress (or deform) differently than the unmodified material. The structure of the material can be altered on a molecular level and/or by disrupting the continuity and/or physical arrangement of portions of the material. "Structure" refers to the physical arrangement of the constituent material that governs mechanical behavior (e.g. how stress is transmitted through the material).

As used herein, the term "Z-dimension" refers to the dimension orthogonal to the length and width of the web or article. The Z-dimension usually corresponds to the thickness of the web or article.

As used herein, the word "zone" refers to an area set off as distinct from surrounding or adjoining areas. Thus, for example, a topsheet comprising uniformly spaced clefts, each of which are the same size, over the entire surface of the topsheet cannot be considered to have any zones of clefts. Moreover, for example, in a topsheet comprising uniformly spaced clefts, each of which are the same size, a single cleft and locally surrounding material cannot be considered a zone of clefts because that single cleft and locally surrounding material are not distinct from surrounding or adjoining areas. Zones can be separated from one another such that there is an absence of like structured material between the zones (i.e. the first structurally modified zone, the second structurally modified zone, the third structurally modified zone, and the fourth structurally modified zone).

Absorbent articles having a topsheet with structurally modified zones are disclosed. The type of physical feature associated with the various structurally modified zones can depend, for example, on the location of the structurally modified zone of the absorbent article. By way of example, structurally modified zones proximate to a main body portion of an absorbent article housing an absorbent core can comprise fibers tufts, while structurally modified zones proximate to a periphery of the absorbent article (such as on wings or flaps) can comprise clefts. With specific regard to clefts formed in a polymer film that covers wings or flaps of an absorbent article, various benefits can be realized. For example, such clefts can convey the perception of quality to a consumer by giving the polymer film a fabric-like appearance and/or a softer texture. In some instances, polymer films with clefts as described herein can feel softer to the touch than polymer films that are merely micro apertured.

Figure 2:
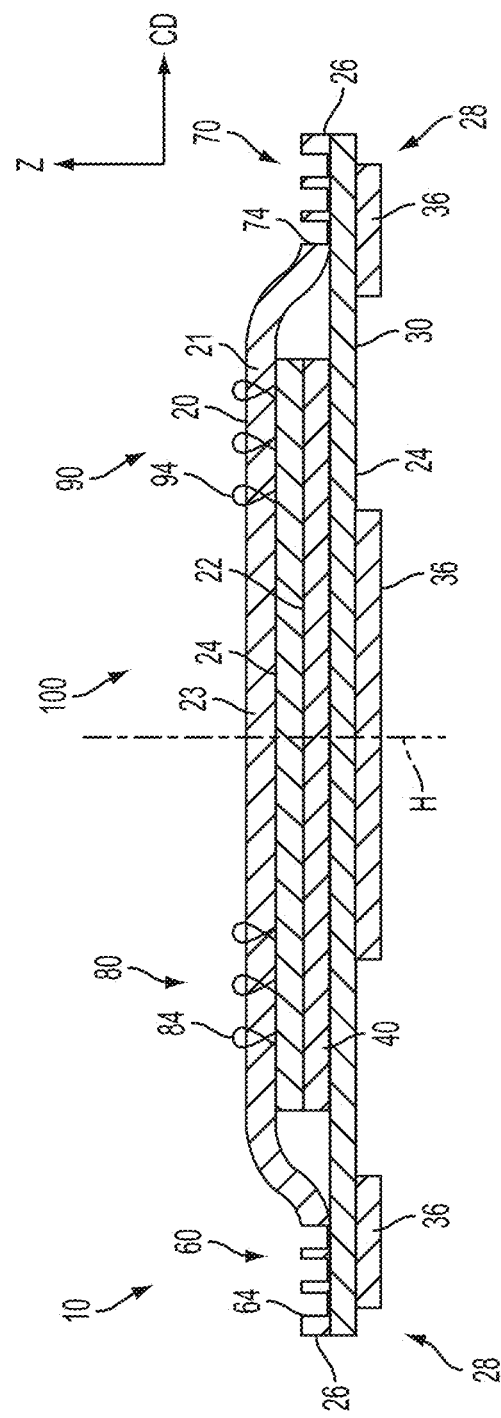
FIG. 2 is an illustration of a cross-sectional view of FIG. 1 taken along line 2-2.

FIG. 1 is an illustration of an embodiment of an absorbent article 10 having a topsheet with different structurally modified zones. FIG. 2 is an illustration of a cross-sectional view of FIG. 1 taken along line 2-2.

An example absorbent article 10 is shown in the form of a sanitary napkin. This type of absorbent article is shown for illustration purpose only as the present disclosure can be used for making a wide variety of other types of absorbent articles. FIG. 1 is a top view absorbent article 10, in a flat-out state, with portions of the structure being cut-away to more clearly show the construction of absorbent article 10. FIG. 2 is a cross-sectional view of the absorbent article of FIG. 1 taken along line 2-2. Absorbent article 10 can comprise a liquid pervious topsheet 20, a fluid impervious backsheet 30, and an absorbent core 40 disposed between topsheet 20 and backsheet 30. As shown in FIG. 2, topsheet 20 is a composite topsheet having an upper layer 21 and a lower layer 22 that are engaged with one another in a layered relationship. By way of example only, the composite or laminate topsheet can comprise a polymer film or nonwoven upper layer, and a nonwoven lower layer. In some embodiments, and as shown in FIG. 2, upper layer 21 extends to the peripheral edge of each of the wings 28, while lower layer 22 does not extend into the wing portions.

Absorbent article 10 and each layer or component thereof can be described as having a body facing surface and a garment facing surface when in a flat-out state. As can be understood by considering the ultimate use for absorbent articles, such as sanitary napkins, diapers, incontinent products and the like, the body facing surfaces are the surfaces of the layers or components that are oriented closer to the body when in use, and the garment facing surfaces are the surfaces that are oriented closer to the undergarment of the wearer when in use. Therefore, for example, as shown in FIG. 2, upper layer 21 of the topsheet 20 has a body facing surface 23 (that can actually be a body contacting surface) and a garment facing surface 24 that is adjacent to topsheet lower layer 22. While a multi-layered topsheet 20 is illustrated, in some embodiments the topsheet is comprised of a single layer. The garment facing surface 24 of backsheet 30, for example, can be oriented closest to, and can contact the wearer's undergarments in use (via a positioning adhesive 36 if used).

Referring to FIG. 2, absorbent article 10 has an absorbent article width measured between the lateral edges 26 measured in the cross direction CD. Absorbent article 10 has a vertical axis H, and a thickness measured in the Z-direction.

Absorbent article 10 can have wings 28, also known as side extensions or flaps, designed to wrap the sides of the crotch region of a user's undergarments and attach thereto. As shown, upper layer 21 of topsheet 20 can extend across the body facing surfaces of the wings 28. Absorbent article 10 and/or wings 28 can have fastening means including attachment components, such as pressure sensitive positioning adhesive 36. As shown, absorbent article 10 has spaced apart strips of positioning adhesive 36 on the garment facing surface 24 of the backsheet 30.

Referring again to FIG. 1, topsheet 20 can has a longitudinal centerline L and a transverse centerline T. Longitudinal centerline L and transverse centerline T define a two-dimensional plane of topsheet 20 prior to use, which, in the embodiment shown, is associated with the machine direction (MD) and cross machine direction (CD) as is commonly known in the art of making articles using production lines. Absorbent article 10 has a length, which is the longest dimension measured parallel to the longitudinal centerline L. The absorbent article has a width, which is the dimension measured in the CD, e.g., parallel to the transverse centerline T. The transverse centerline T intersects the longitudinal centerline L at mid-length of the longitudinal centerline L. The width of absorbent article 10 can vary or be substantially constant along the length of the absorbent article 10. For descriptive purposes, absorbent article 10 has a longitudinal centerline and transverse centerline taken to be coincident with topsheet longitudinal centerline L and topsheet transverse centerline T, respectively. The actual longitudinal centerline and the transverse centerline of the absorbent article 10 need not be coincident with the longitudinal centerline L and transverse centerline T of the topsheet 20.

The topsheet can be, for example, a film, a nonwoven, or a laminate. A laminate topsheet can comprise two layers of film, two layers of nonwoven, or a layer of nonwoven with a film. The topsheet can include a microtextured polymer film. The microfeatures can, for example, be micro apertures or micro bubbles, examples of which are disclosed in U.S. Pat. No. 7,402,732, issued to Stone et al. and U.S. Pat. No. 4,839,216 issued to Curro et al.; U.S. Pat. No. 4,609,518 issued to Curro et al., and U.S. Pat. No. 4,609,518 issued to Curro et al. The microfeatures can be raised portions. The microfeatures are generally not visible to the unaided eye of a person having 20/20 vision from a distance of 30 cm in lighting at least equal to the illumination of a standard 100 watt incandescent white light bulb. Micro apertures and/or other microtexturing can be formed prior to processing as described herein.

As shown in FIG. 1, topsheet 20 comprises a plurality of portions or zones. The illustrated embodiment is shown having a first portion 60, a second portion 70, a third portion 80, a fourth portion 90, and a fifth portion 100. The first and second portions 60, 70 of topsheet 20 are proximate wings 28 and differ in structure from the third, fourth, and fifth portions 80, 90, and 100 of topsheet 20. The third, fourth, and fifth portions 80, 90, 100 can generally overlap absorbent core 40. In embodiments having a multi-layered topsheet 20, the third, fourth, and fifth portions 80, 90, 100 can generally overlap all or a portion of topsheet lower layer 22.

As used herein, one or more of the first, second, third, and fourth structurally modified zones 62, 72, 82, 92 are referred to generically as the structurally modified zone(s). The structurally modified zones can be integral with the topsheet 20. That is, the topsheet 20 is comprised one or more of the first, second, third, and fourth structurally modified zones 62, 72, 82, 92. The structurally modified zones can be comprised of a continuous web or webs of material. Each of the structurally modified zones can be comprised of the same precursor materials or some may be comprised of the same precursor materials and some comprised of different precursor material. For example, the third and fourth structurally modified zones 82, 92 can be comprised of two or more layers engaged with one another in a layered relationship, for example, as in a laminate. As is to be appreciated, the particular shape and configuration of the structurally modified zones illustrated in FIG. 1 are merely exemplary and are not intended to be limiting.

First portion 60 can comprise a first structurally modified zone 62 that comprises a plurality of clefts 64. Second portion 70 can comprise a second structurally modified zone 72 that comprises a plurality of clefts 74. The plurality of clefts 64 can be structurally similar or dissimilar to the plurality of clefts 74.

Clefts 64 and 74 are schematically illustrated in FIG. 1 and not necessarily drawn to scale. Also, while adjacent structurally modified zones are shown to be laterally separated in FIG. 2 by a non-structurally modified zone, in other embodiments the lateral separation between adjacent structurally modified zones is minimized or eliminated. Clefts 64 and 74 defining, at least in part, the structurally modified zones can have different sizes and/or be arranged in different patterns to deliver different performance benefits, such as comfort or managing bodily exudates, to different portions of the body. For example, clefts 64 and 74 can be arranged to provide the wings 28 with a desired texture and/or aesthetic.

The first and second structurally modified zones 62, 72 can comprise more than about 2% of the area of the wings 28, the area of the wings 28 being measured in the plane of the longitudinal centerline L and transverse centerline T of the topsheet 20 and defined by the portions of the topsheet 20 configured to be folded or wrapped during use. The first and second structurally modified zones 62, 72 can comprise more than about 20% of the area of the wings 28. The first and second structurally modified zones 62, 72 can comprise more than about 50% of the area of the wings 28. The first and second structurally modified zones 62, 72 can comprise more than about 70% of the area of the wings 28. The first and second structurally modified zones 62, 72 can comprise more than about 90% of the area of the wings 28. The first and second structurally modified zones 62, 72 can comprise more than about 99% of the area of the wings 28.

Figure 3:
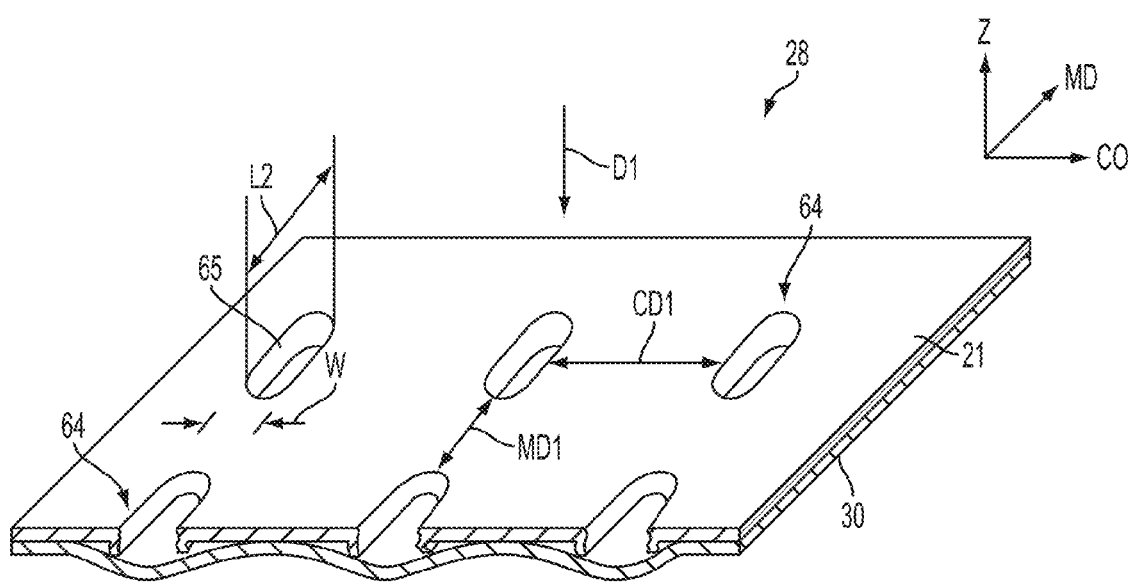
FIG. 3 is a perspective view of a portion of a wing of an absorbent article that comprises clefts.

FIG. 3 is a perspective view of the first portion 60 of wing 28 that comprises clefts 64. Clefts 64 protrude in the Z-direction and can be formed by urging discrete portions of the topsheet upper layer 21 in a first direction, as indicated by arrow D1. Clefts 64 can be formed into the upper layer 21 prior to the upper layer 21 being joined with the backsheet 30. Clefts 64 have a sidewall 65 that extends towards, and in some instances contact backsheet 30. In other embodiments, cleft sidewalls 65 can extend away from backsheet 30. Example manufacturing processes are described in more detail below with reference to FIGS. 12-14. The clefts can be positioned in the CD-MD plane in any suitable arrangement. In some embodiments, the clefts are separated from adjacent clefts in the cross direction by a distance (shown as distance CD1) of about 1 mm or less. The clefts can be separated from adjacent clefts in the cross direction by other distances, such as about 2 mm, about 5 mm, about 10 mm, about 20 mm, or greater or less distances. In some embodiments, clefts 64 are separated from adjacent clefts in the machine direction by a distance (shown as distance MD1) of about 1 mm or less. The clefts can be separated from adjacent clefts in the machine direction by other distances, such as about 2 mm, about 5 mm, about 10 mm, about 20 mm, or greater or less distances. The distance CD1 can be greater or less than the distance MD1.

While the clefts illustrated in FIG. 3 have generally oblong shapes, in other embodiments clefts can have other shapes, such as rectangular, circular, diamond, triangular, and so forth. In some embodiments, a plurality of different shaped clefts can be formed into the wing materials. The clefts can have an aspect ratio (ratio of longest dimension to shortest dimension, both measured in the MD-CD plane) greater than 1. In the illustrated embodiment, the length of the cleft in the machine direction (shown as length L2) can be in the range of about 1 mm to about 4 mm. The length L2 can be other lengths, such as in the range of about 2 mm to about 3 mm. The length L2 can also be greater than 4 mm. The width of the cleft in the cross direction (shown as length W) can be in the range of about 0.3 mm to about 2 mm. The width W can be other lengths, such as in the range of about 0.75 mm to about 1.25 mm, for example.

Figure 4:
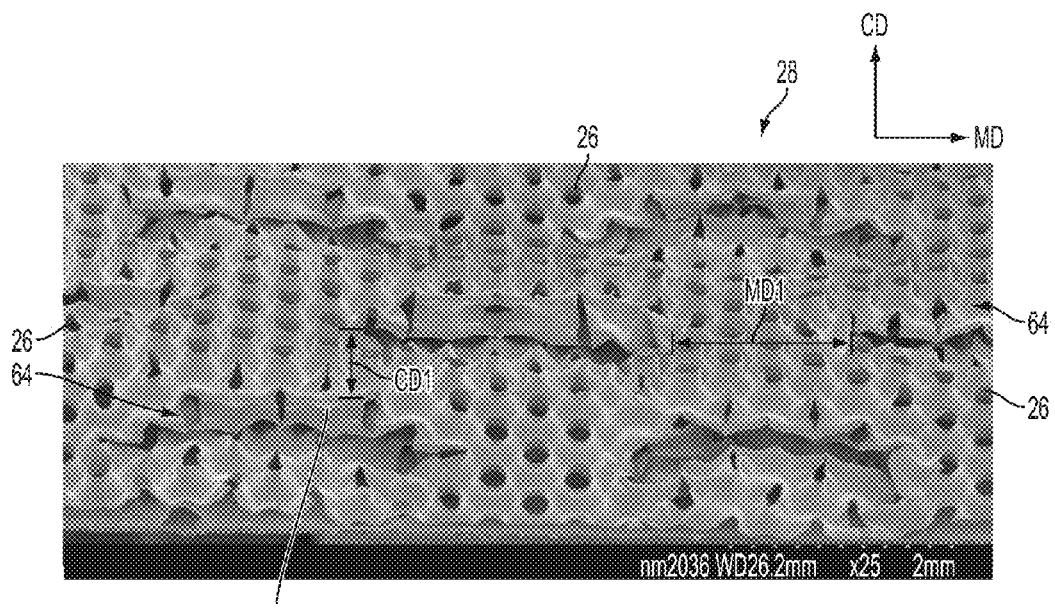
FIG. 4 is a perspective view of a micrograph of a portion of a wing of an absorbent article at a magnification factor of 25.
Figure 5:
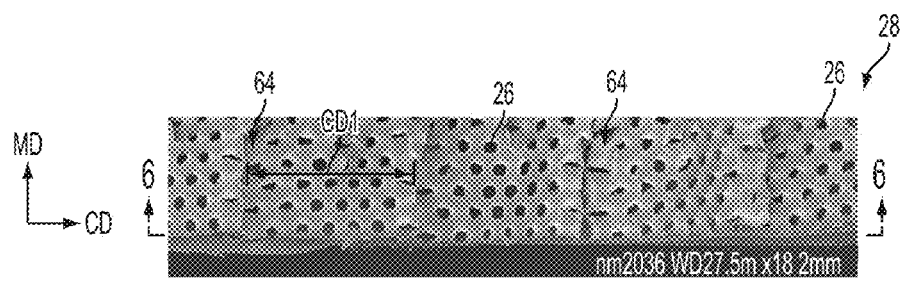
FIG. 5 is a top view of the micrograph of an enlarged portion of wing of FIG. 4 at a magnification factor of 18.
Figure 6:
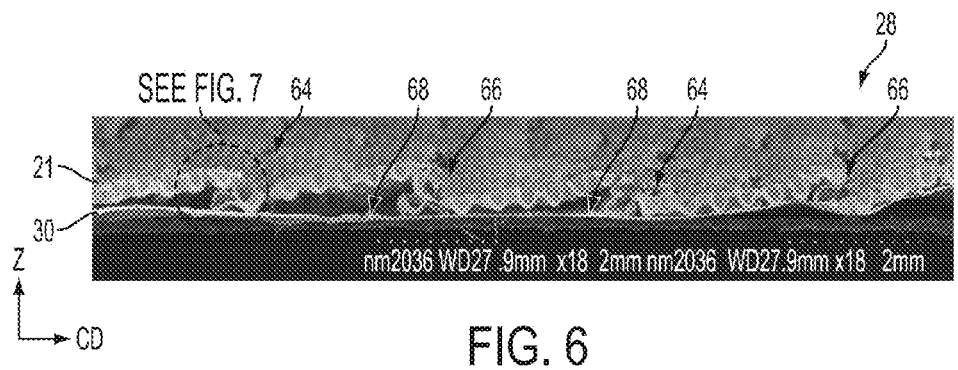
FIG. 6 is a cross-sectional view of FIG. 5 taken along line 6-6 showing a plurality of clefts.
Figure 7:
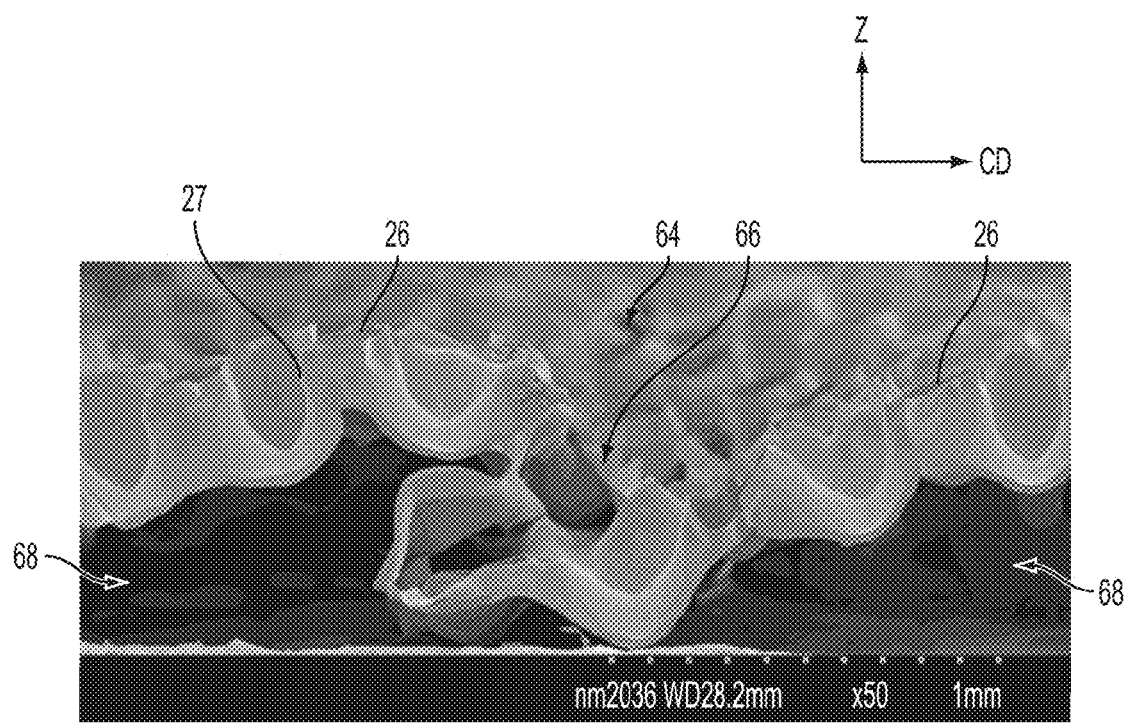
FIG. 7 is a micrograph of one cleft shown in FIG. 6 at a magnification factor of 50.

FIGS. 4-7 are micrographs of the first portion 60 of wing 28 that comprises clefts 64. FIG. 4 is a top perspective view of wing 28 at a magnification factor of 25. FIG. 5 is a top view of wing 28 and FIG. 6 is a cross-sectional view of FIG. 5 taken along line 6-6, each micrograph having a magnification factor of 18. FIG. 7 is a micrograph of the cleft shown in FIG. 6 at a magnification factor of 50. Wing 28 shown in FIGS. 4-7 comprises an upper layer 21 of the topsheet that has micro apertures 26 in addition to clefts 64. Micro apertures 26 include aperture sidewalls 27 that generally extend in a different direction (for example, an opposite direction) that cleft sidewalls 65. As can be seen in FIGS. 4-6, the cleft sidewalls 65 can be partially collapsed, buckled, folded, or tucked. And cleft sidewalls 65, as shown in FIG. 4, can contain some of the micro apertures 26.

Referring now to FIGS. 6-7, the clefts 64 facilitate the formation of various cavities or voids in the wing 28. A first void 66 is defined by the portions of the body facing surface 23 (FIG. 2) of the upper layer 21 that are deformed to define the cleft 64. A second void 68 can be formed when the upper layer 21 is joined with the backsheet 30. Specifically, void 68 is defined in the Z-direction by backsheet 30 (FIG. 6) and upper layer 21 and is defined in the cross direction by the garment facing surface 24 (FIG. 2) of adjacent clefts. Voids 66 and 68 may help to visually convey the depth and/or absorbency of the wing 28 to a consumer, while also provide a desired texture to wing 28.

Referring again to FIGS. 1 and 2, the third topsheet portion 80 can comprise a third structurally modified zone 82. And the fourth topsheet portion 90 can comprise a fourth structurally modified zone 92. The fifth portion 100 can include a variety of structurally modified features, both those described herein and those known to the skilled artisan.

Figure 8:
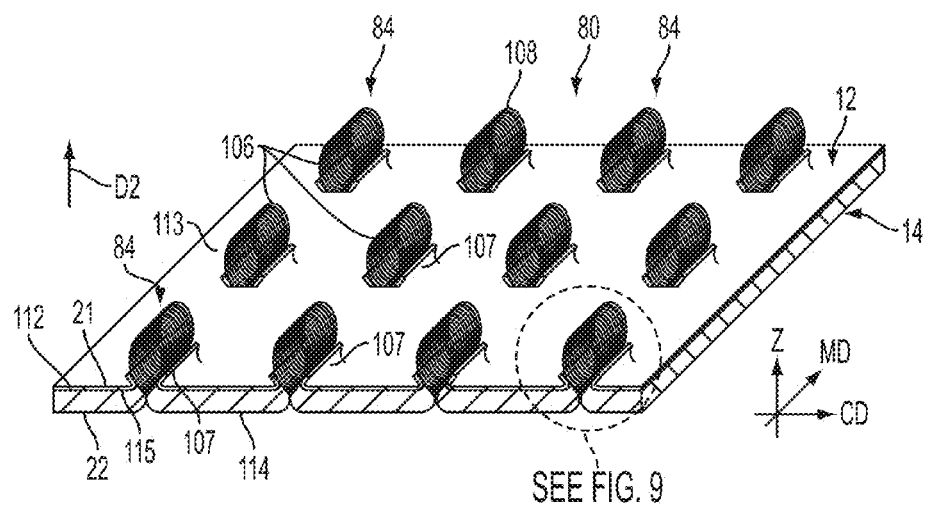
FIG. 8 is a perspective view of a portion of an absorbent article comprising film ruptures and fiber tufts.

Third structurally modified zone 82 and fourth structurally modified zone 92 can contain features that are different than the clefts. The third and fourth structurally modified zones 82 and 92 are generally formed by urging lower layer 22 into and optionally through upper layer 21. In some embodiments, the third and fourth structurally modified zones can contain a plurality of ruptures 84 in upper layer 21, as is shown in FIG. 8. The rupturing of upper layer 21 can result in web material flaps 107. Fiber tufts 106 are shown extending through ruptures 84.

Figure 9:
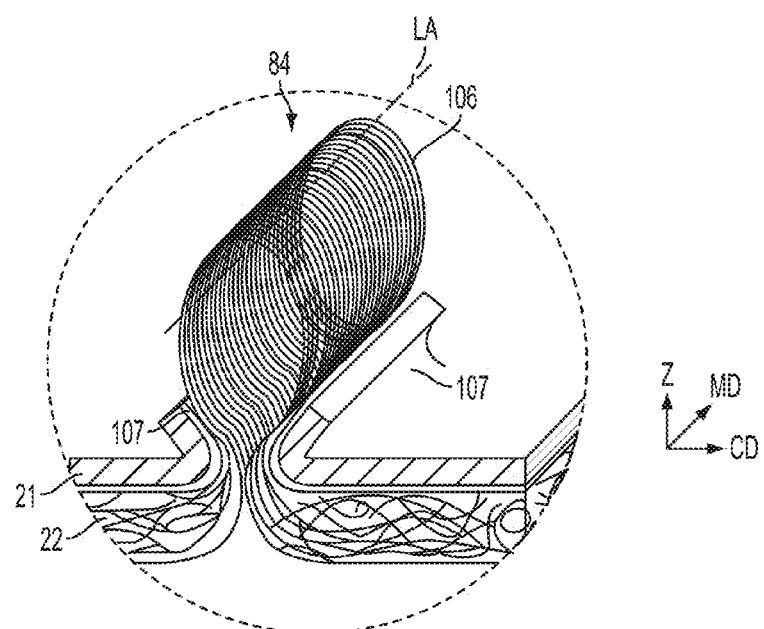
FIG. 9 is an enlarged view of a film rupture and fiber tuft extending therethrough, as indicated in FIG. 8.

FIG. 9 is an enlarged view of a rupture 84 and fiber tuft 106. In the illustrated embodiment, each rupture 84 comprises a tuft 106 formed when the lower layer 22 is pushed into the upper layer 21 and protrudes through apertures therein. The upper and lower layers 21, 22 can be referred to herein as generally planar, two-dimensional precursor webs. Either precursor web can be a film, a nonwoven, or a woven web. Upper layer 21 and the lower layer 22 (and any additional webs) can be joined with or without adhesive, thermal bonding, ultrasonic bonding and the like.

Figure 10:
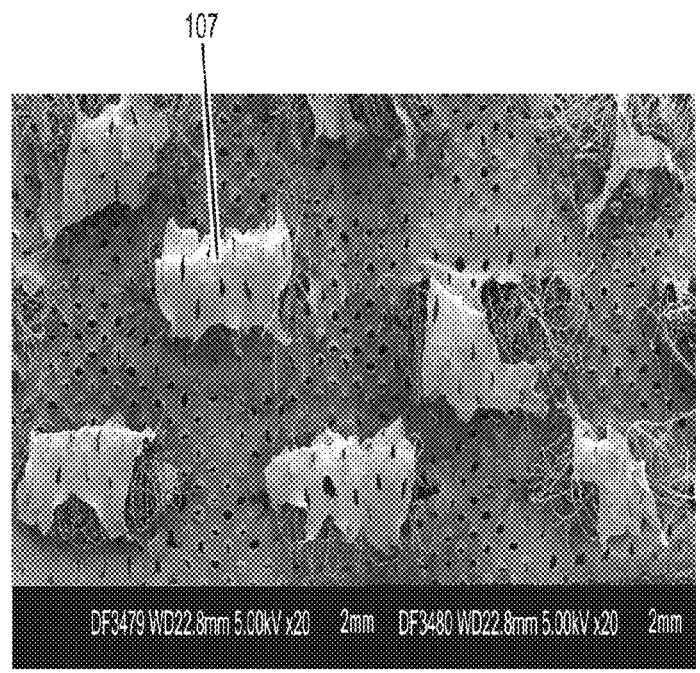
FIG. 10 is a plan view of another structurally modified web wherein displaced polymer film sections form a partial cap over underlying fiber tufts.

FIG. 10 is a photomicrograph of another structurally modified web embodiment, wherein the web material flaps 107 remain somewhat intact to form caps/partial caps over underlying fiber tufts 106 (shown in FIGS. 8 and 9).

Referring again to FIG. 9, third portion 80 has a first side 12 and a second side 14, the term "sides" being used in the common usage of generally planar two-dimensional webs, such as paper and films that have two sides when in a generally flat condition. Lower layer 22 has a lower layer first surface 112 and a lower layer second surface 114. Upper layer 21 has an upper layer first surface 113 and an upper layer second surface 115. The lower layer 22 can be a nonwoven web comprised of substantially randomly oriented fibers, a polymer film, or a woven web. By "substantially randomly oriented" is meant that, due to processing conditions of the precursor web, there may be a higher amount of fibers oriented in the MD than the CD, or vice-versa. The upper layer 21 can be a nonwoven web similar to the lower layer 22, or a polymer film or an apertured polymer film, such as a polyethylene film. The upper layer 21 can also comprise micro apertures (see, for example, FIG. 10).

In one embodiment, the first side 12 of the third portion 80 is defined by exposed portions of the upper layer first surface 113 and one or more discrete fiber tufts 106, which are integral extensions of the fibers of a nonwoven lower layer 22. The fiber tufts 106 can protrude through ruptures in the second precursor web 121. As shown in FIG. 8, each tuft 106 can comprise a plurality of looped fibers 108 extending through the upper layer 21 and outwardly from the upper layer first surface 113 thereof.

Fiber tufts can be formed by urging fibers out-of-plane along the Z-axis in a second direction, as indicated by arrow D2 in FIG. 8, at discrete, localized, portions of lower layer 22. Second direction D2 can be different than the first direction D1 (FIG. 3). In some embodiments, first direction D1 is substantially opposite to second direction D2. The lower layer can be a fibrous woven or nonwoven web comprising elastic or elastomeric fibers. Elastic or elastomeric fibers can be stretched at least about 50% and return to within 10% of their original dimension. The fiber tufts can be formed from elastic fibers if the fibers are simply displaced due to the mobility of the fiber within the nonwoven or if the fibers are stretched beyond their elastic limit and are plastically deformed. In some embodiments, non-elastic fibers from the nonwoven can form suitable structures.

The topsheet upper layer can be virtually any web material, the only requirement being that it have sufficient integrity to be formed into the laminate by the process described below, and that it have elongation properties relative to the lower layer 22, such that upon experiencing the strain of fibers from the lower layer 22 being urged out-of-plane in the direction of the upper layer 21, the upper layer 21 will be urged out of plane (e.g. by stretching) or rupture (e.g. by tearing due to extensional failure). If rupture occurs, apertures can be formed at the rupture locations. Portions of the lower layer 22 can extend through apertures/ruptures 84 (i.e., "push through" or protrude through) in the upper layer 21 to form fiber tufts 106 on the first side 12 of the third portion 80. In one embodiment the upper layer 21 is a polymer film. The upper layer 21 can also be a woven textile web, a nonwoven web, a polymer film, an apertured polymer film, a paper web, or the like.

The looped fibers 108 can be substantially aligned such that the tuft 106 has a distinct linear orientation and a long axis LA, as shown in FIG. 9. In the embodiment shown in FIG. 9, the long axis LA is parallel to the MD. Fiber tufts 106 can have a symmetrical shape in the MD-CD plane, such as a circular shape or square shape. Fiber tufts 106 can have an aspect ratio (ratio of longest dimension to shortest dimension, both measured in the MD-CD plane) greater than 1. In one embodiment, all the spaced apart fiber tufts 106 have generally parallel long axes LA. The number of tufts 106 per unit area of the third portion 80, i.e., the area density of the fiber tufts 106, can be varied from about 1 tuft/$cm^2$ to about 100 tufts/$cm^2$. There can be at least about 10, or at least about 20 tufts/$cm^2$. U.S. Pat. Nos. 7,993,317 and 8,058,501 provide additional details regarding laminate webs comprising tufts and apertures.

Figure 11:
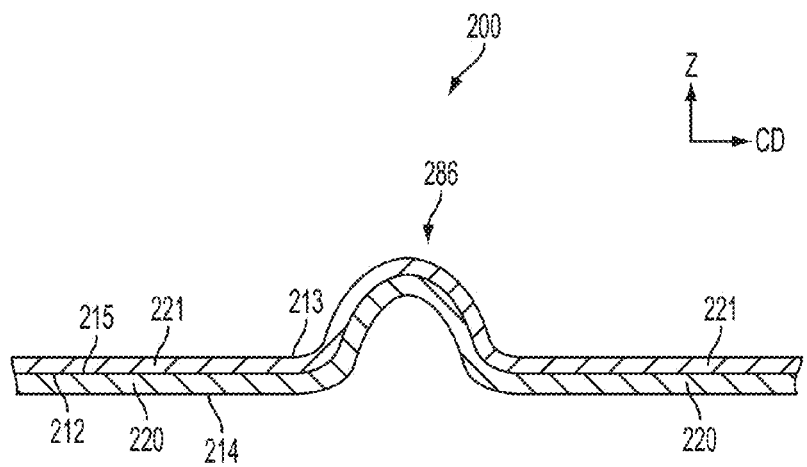
FIG. 11 is a cross-sectional view of a structurally modified web having deformed and nested web layers.

As noted above, the topsheet upper and lower layers can be made from a variety of materials. When the upper layer is made from a polymeric film and the lower layer is made from a nonwoven, the resulting structurally modified features are typically configured as shown in FIGS. 8-10. When both the upper and lower layers are nonwovens, the properties of the upper layer and/or fibers of the same may result in the upper layer not rupturing when the lower layer fibers are urged into the upper layer. By way of example only, FIG. 11 is a cross sectional side view of a structurally modified web 200 comprising a lower nonwoven web 220 and an upper nonwoven web 221, each of which are referred to herein as generally planar, two-dimensional precursor webs. Lower nonwoven web 220 has a first surface 212 and a second surface 214. Upper nonwoven web 221 has a first surface 213 and a second surface 215. The structurally modified web 200 has a machine direction (MD) and a cross machine direction (CD) as is commonly known in the art of web manufacture. Lower nonwoven web 220 can be a nonwoven web comprised of substantially randomly oriented fibers. By "substantially randomly oriented" is meant that, due to processing conditions of the precursor web, there may be a higher amount of fibers oriented in the MD than the CD, or vice-versa. Upper nonwoven web 221 can be similar or dissimilar to lower nonwoven web 220. The upper and lower nonwoven webs can be joined with or without adhesive, thermal bonding, ultrasonic bonding and the like. Lower nonwoven web 220 and upper nonwoven web 221 can correspond to, for example, the lower layer 22 and the upper layer 21, respectively, of topsheet 20, as shown in FIGS. 1-2.

In FIG. 11, the out-of-plane deformation 286 is formed when the upper nonwoven web 221 merely deforms or stretches in the region of induced strain during manufacturing, but does not actually fail. Deformation 286 illustrated in FIG. 11 is in effect the lower nonwoven web 220 nested in the indented upper nonwoven web 221.

Figure 12:
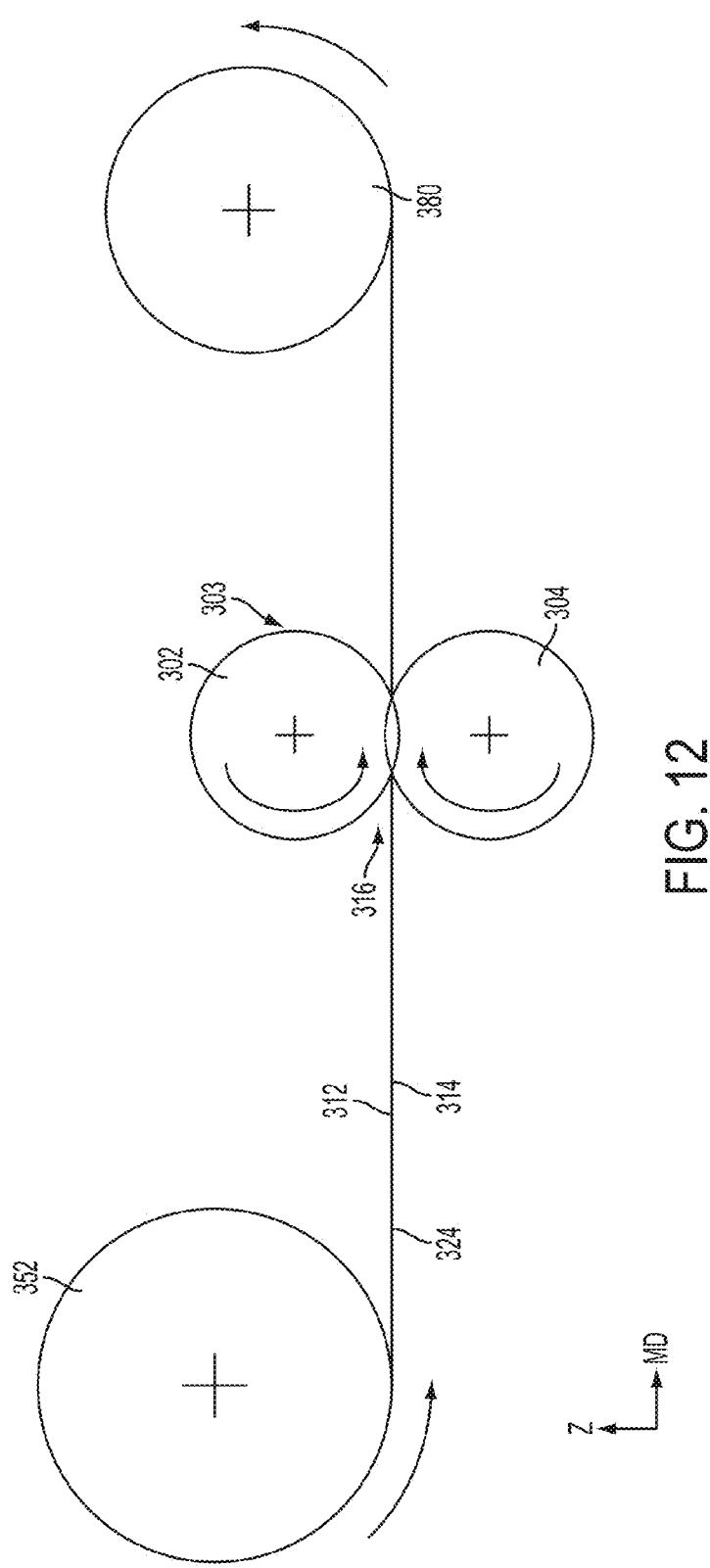
FIG. 12 is a schematic of an apparatus for forming a structurally modified web of material.
Figure 13:
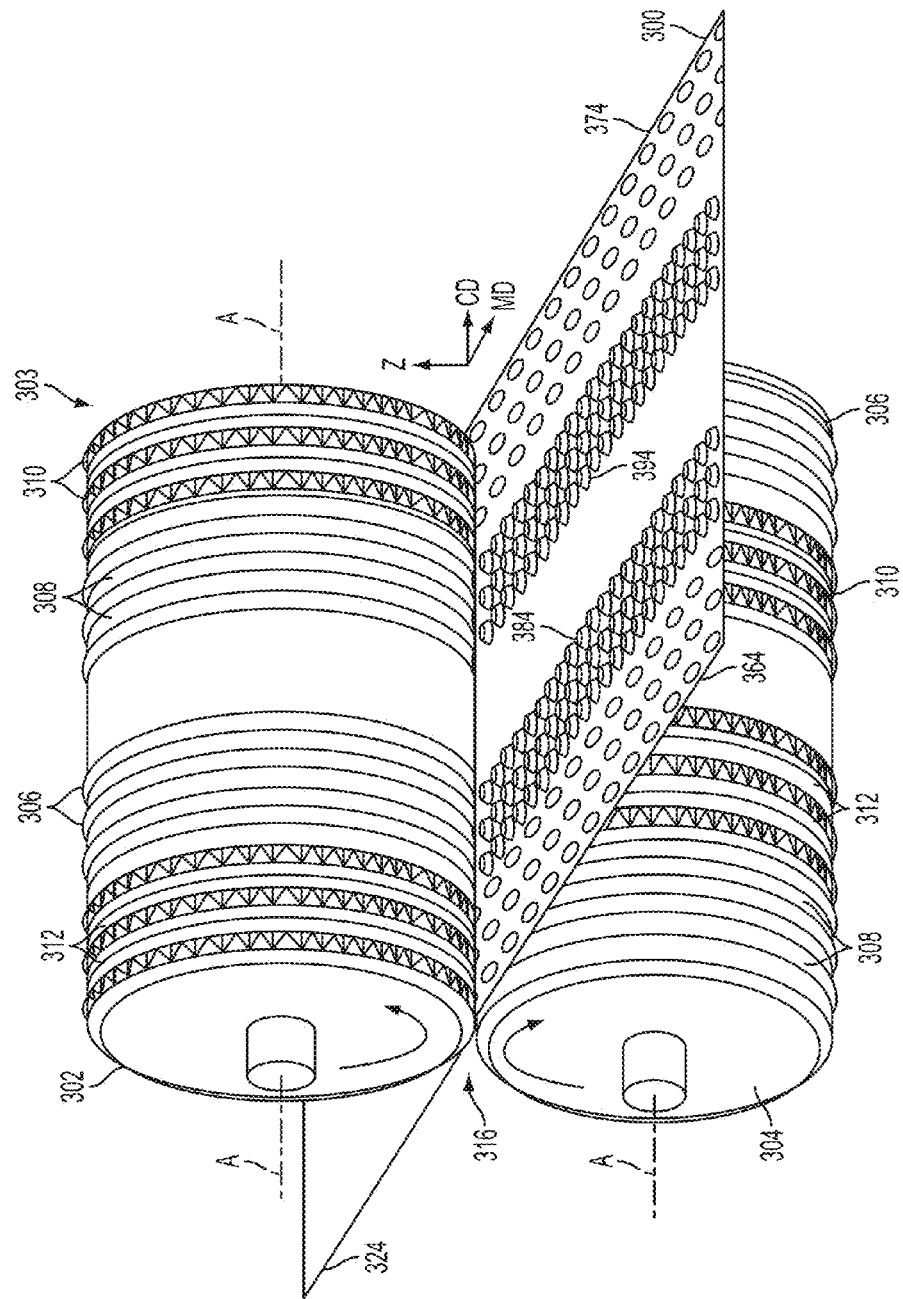
FIG. 13 is a schematic of an apparatus for forming a structurally modified a web of material.

FIGS. 12 and 13 provide a schematic of an apparatus for forming a structurally modified web 300. The structurally modified web 300 can be a film, a nonwoven material, and can have one or more layers. The structurally modified web 300 can be formed from a generally planar, two dimensional precursor web 324 having a first side 312 and a second side 314. The precursor web 324 can be, for example, a polymer film, a nonwoven web, a woven fabric, a paper web, a tissue paper web, or a knitted fabric, or a multilayer laminate of any of the aforementioned. In a composite or laminate structure, the first side 312 of the precursor web of material 324 is the first side of one of the outermost layers or plies opposing one another, and the second side 314 is the second side of the other outermost layer or ply.

The precursor web 324 can be a polymeric film web. And the polymeric film can be microtextured polymer film. The microfeatures can, for example, be microapertures or micro bubbles, examples of which are disclosed in U.S. Pat. No. 7,402,732, issued to Stone et al. and U.S. Pat. No. 4,839,216 issued to Curro et al.; U.S. Pat. No. 4,609,518 issued to Curro et al., and U.S. Pat. No. 4,609,518 issued to Curro et al. The microfeatures can be raised portions. Polymeric film can be deformable. Deformable, as used herein, describes a material which, when stretched beyond its elastic limit, will substantially retain its newly formed conformation. Polymeric film webs can include materials normally extruded or cast as films such as polyolefins, nylons, polyesters, and the like. Such films can be thermoplastic materials such as polyethylene, low density polyethylene, linear low density polyethylene, polypropylenes and copolymers and blends containing substantial fractions of these materials.

The precursor web 324 can be a nonwoven web. For nonwoven precursor webs 324, the precursor web 324 can comprise unbonded fibers, entangled fibers, tow fibers, or the like. Fibers can be extensible and/or elastic, and may be pre-stretched for processing. Fibers of the precursor web 324 can be continuous, such as those produced by spunbonded methods, or cut to length, such as those typically utilized in a carded process. Fibers can be absorbent, and can include fibrous absorbent gelling materials. Fibers can be bicomponent, multiconstituent, shaped, crimped, or in any other formulation or configuration known in the art for nonwoven webs and fibers. The precursor web 324 can comprise a first layer and second layer. For example the first layer can be a polymer film web and the second layer can be a nonwoven web. In some embodiments, the nonwoven web does not extend across the entire polymer film web in the cross direction.

The supply roll 352 rotates in the direction indicated by the arrow in FIG. 12 as the precursor web 324 is moved in the machine direction by means known in the art, including over or around any of various idler rollers, tension-control rollers, and the like to the nip 316 of a pair of counter-rotating rolls 302 and 304. The rolls 302 and 304 can comprise a forming apparatus 303. The structurally modified web 300 can be taken up on wind up roll 380, as shown, or directly provided to subsequent downstream processing, as is known in the art.

There are a variety of approaches for creating structurally modified webs. Factors that can influence the approach selected for creating structural modifications include, but are not limited to, whether the precursor web 324 is a nonwoven, a polymeric film, a laminate and the desired geometry of the cleft, the desired processing speed, and the amount of control of the process that is desired. Referring to FIG. 13, there is shown in more detail the portion of the apparatus shown in FIG. 12 that can form structurally modified web 300 having a plurality of structural modification types in the cross direction. The forming apparatus 303 can comprise a pair intermeshing rolls 302 and 304 (as shown in FIGS. 12 and 13), each rotating about an axis A, the axes being parallel and in the same plane. Forming apparatus 303 can be designed such that precursor web 324 remains on roll 304 through a certain angle of rotation. FIG. 13 shows in principle what happens as precursor web 324 goes straight through nip 316 on forming apparatus 303 and exits as structurally modified web 300. Precursor web 324 or structurally modified web 300 can be partially wrapped on either of rolls 302 or 304 through a predetermined angle of rotation prior to (for precursor web 324) or after (for structurally modified web 300) nip 316.

The forming apparatus 303 can be configured to form structural modifications of a first type concurrently with structural modifications of a second type. The particular placement of the structural modifications on the precursor web 324 can depend on, for example, the arrangement of the absorbent article in which the structurally modified web 300 will ultimately be incorporated. For example, a first type of structural modifications may be formed into a region of the precursor web which will form a wing of an absorbent article (such as absorbent article 10 of FIG. 1) and second type of structural modifications may be formed into a region of the precursor web which will be proximate to a main body portion of an absorbent article. In the illustrated embodiment, the structural modifications 364, 374, 384, 394 formed by the forming apparatus 303 include structural modifications formed by urging discrete portions of the precursor web 324 in a first direction while concurrently urging other discrete portions of the precursor web 324 in a different, opposite direction. More specifically, clefts 364 and 374 are formed by the forming apparatus 303 urging discrete portions of the precursor web 324 in a first direction and ruptures 384 and 394 are formed by the forming apparatus 303 urging discrete portions of the precursor web 324 in a second direction. In the illustrated embodiment, the first and second directions generally extend in opposite directions that are parallel to the Z-direction. The structurally modified web 300 can be used as a topsheet for an absorbent article comprising wings and an absorbent core in a downstream process, with the portion of the structurally modified web 300 comprising clefts 364 and 374 positioned proximate to the wings of an absorbent article and the portion of the structurally modified web 300 comprising web ruptures 384 and 394 positioned proximate to an absorbent core.

Rolls 302 and 304 can each comprise a plurality of ridges 306 and corresponding valleys 308 which can extend unbroken about the entire circumference of the corresponding roll. Depending on what kind of structural modifications desired, ridges 306 can have portions removed, such as by etching, milling or other machining processes, such that some or all of ridges 306 are not circumferentially continuous, but have breaks or gaps. Ridges 306 can be spaced apart from one another along the axis A of the roll 302 and the roll 304. For instance, as shown, the middle third of roll 302 and roll 304 can be smooth and outer portions of the roll 302 and roll 304 can have a plurality of ridges that are spaced apart from one another. The smooth, central portion results in the web 300 having an un-modified central portion. The breaks or gaps, in either the circumferential direction, axial direction, or both directions, can be arranged to form a pattern, including geometric patterns such as circles or diamonds. The rolls 302 and 304 can each comprise a plurality of rows of circumferentially-extending ridges that have been modified to be rows of circumferentially-spaced teeth 310 that extend in spaced relationship about at least a portion of the corresponding roll. The individual rows of teeth 310 can be separated by corresponding grooves 312. In operation, rolls 302 and 304 intermesh such that the ridges 306 of one roll extend into the grooves 312 of the other roll and the teeth 310 of one roll extend into the valleys 308 of the other roll. The teeth 310 on one roll 302, 304 may be different than the teeth 310 on the other roll 302, 304 in order to form different types of structural modifications. Both or either of rolls 302 and 304 can be heated by means known in the art such as by incorporating hot oil filled rollers or electrically-heated rollers. Alternatively, both or either of the rolls may be heated by surface convection, induction, or by surface radiation.

Figure 14:
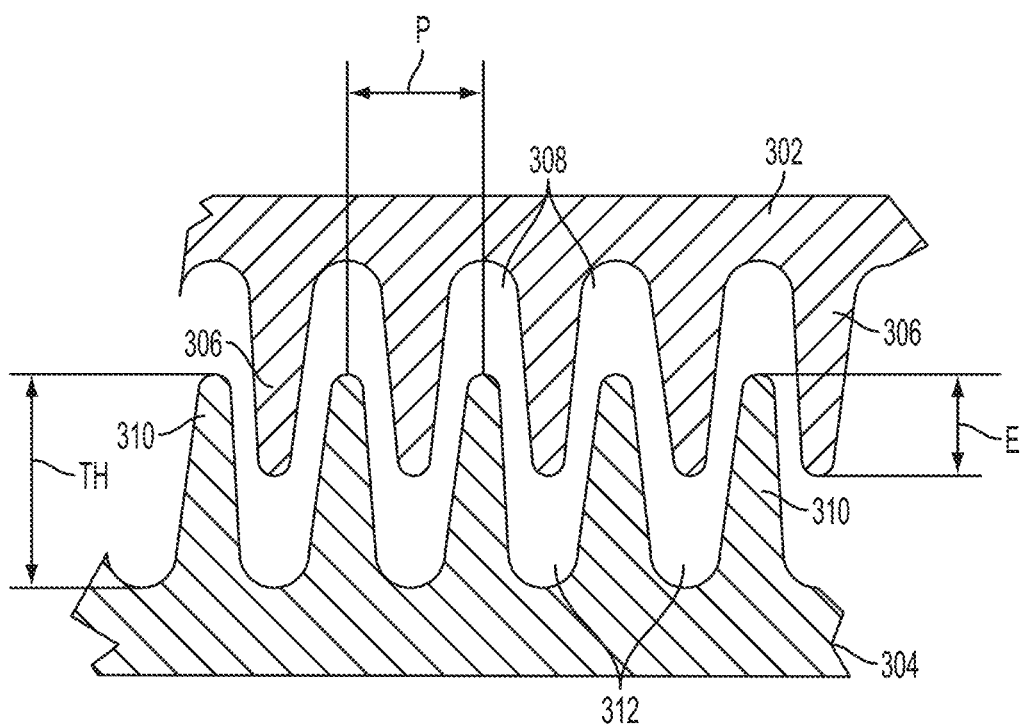
FIG. 14 is a schematic of exemplary intermeshing rolls.

A schematic of a cross section of a portion of the intermeshing rolls 302 and 304 including ridges 306 and representative teeth 310 is shown in FIG. 14. As shown, teeth 310 have a tooth height TH (note that TH can also be applied to ridge 306 height and tooth height and ridge height can be equal or non-equal) and a tooth-to-tooth spacing (or ridge-to-ridge spacing) referred to as the pitch P. As shown, depth of engagement, (DOE), E is a measure of the level of intermeshing of rolls 302 and 304 and is measured from tip of ridge 306 to tip of tooth 310. The depth of engagement E, tooth height TH, and pitch P can be varied as desired depending on the properties of precursor web 324 and the desired characteristics of structurally modified web 300 (FIG. 13). The rolls 302 and 304 can be made of tool steel, wear resistant stainless steel, ceramics, or other durable materials.

Referring to FIGS. 12-14, as precursor web 324 goes through the nip 316, the teeth 310 of roll 302 and roll 304 enter valleys 308 of roll 302 and roll 304 to simultaneously urge material out of the plane of precursor web 324 to form structural modifications 364, 374, 384, 394. In effect, teeth 310 "push" through precursor web 324. As the tip of teeth 310 push through precursor web 324 the web material can be urged by the teeth 310 out of the plane of precursor web 324 and can be stretched and/or plastically deformed in the Z-direction, creating out-of-plane geometry.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 millimeters" is intended to mean "about 40 millimeters."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article, comprising:
   a topsheet, a backsheet opposing the topsheet, and an absorbent core disposed between the topsheet and the backsheet, the topsheet comprising a polymeric film, a longitudinal centerline, and a transverse centerline perpendicular thereto;
   one or more wings each extending along a respective axis parallel to the transverse centerline, each wing defining a first portion of the topsheet and a second portion of the topsheet, wherein the first and second portions of the topsheet are on opposing sides of the longitudinal centerline, and wherein the first portion comprises a first structurally modified zone and the second portion comprises a second structurally modified zone;
   wherein the topsheet comprises a third portion and a fourth portion, wherein the third and fourth portions of the topsheet are on opposing sides of the longitudinal centerline, and wherein the third and fourth portions are each positioned intermediate the first and second portions along an axis parallel to the transverse centerline, wherein the third portion comprises a third structurally modified zone and the fourth portion comprises a fourth structurally modified zone; and
   wherein the first structurally modified zone comprises a first plurality of clefts and the second structurally modified zone comprises a second plurality of clefts, the first and second plurality of clefts being formed by urging discrete portions of the polymeric film in a direction towards the backsheet to define cleft sidewalls that are buckled or tucked underneath the topsheet and positioned between the polymeric film and the backsheet and the third and fourth structurally modified zones comprise a plurality of film ruptures, the plurality of film ruptures being formed by urging discrete portions of the polymeric film in a direction that is away from the backsheet to define polymeric film flaps that extend outward from the topsheet.

2. The absorbent article of claim 1, wherein the topsheet further comprises an underlying nonwoven layer.

3. The absorbent article of claim 2, wherein the polymeric film extends outward beyond the periphery of the underlying nonwoven layer.

4. The absorbent article of claim 2, wherein fibers from the underlying nonwoven extend into and/or through at least some of the plurality of film ruptures.

5. The absorbent article of claim 1, wherein at least some of the first portion and the second portion of the topsheet are directly adjacent the backsheet.

6. An absorbent article, comprising:
a main body having a longitudinal centerline and a transverse centerline, the main body comprising an absorbent core;
first and second wings extending in directions parallel to the transverse centerline and outwardly from the main body on opposing sides of the longitudinal centerline;
a topsheet comprising a polymeric film and extending across the first wing, the main body, and the second wing, wherein the topsheet comprises a first wing portion, a second wing portion and a main body portion; and
a backsheet extending across the first wing, the main body, and the second wing;
wherein the first and second wing portions of the topsheet comprise a plurality of clefts that comprise cleft sidewalls that are buckled or tucked underneath the topsheet and positioned between the polymeric film and the backsheet.

7. The absorbent article of claim 6, wherein the first and second wing portions of the topsheet further comprise a plurality of apertures that comprise aperture sidewalls, and wherein at least some of the aperture sidewalls extend in a direction away from the backsheet.

8. The absorbent article of claim 7, wherein the cleft sidewalls comprise some of the plurality of apertures.

9. The absorbent article of claim 6, wherein the topsheet further comprises a nonwoven that underlies the polymeric film, and wherein the nonwoven does not extend laterally to the same extent as the first and second wing portions.

10. An absorbent article, comprising:
a main body having a longitudinal centerline and a transverse centerline, the main body comprising an absorbent core;
first and second wings extending in directions parallel to the transverse centerline and outwardly from the main body on opposing sides of the longitudinal centerline;
a topsheet comprising a polymeric film and extending across the first wing, the main body, and the second wing, wherein the topsheet comprises a first wing portion, a second wing portion and a main body portion; and
a backsheet extending across the first wing, the main body, and the second wing;
wherein the first and second wing portions of the topsheet comprise a plurality of apertures that comprise aperture sidewalls extending unconstrained in a first direction outward from the topsheet; and
wherein the first and second wing portions of the topsheet comprise a plurality of clefts that comprise cleft sidewalls extending in a second direction that is different from the first direction, wherein the second direction is substantially parallel to the topsheet and/or backsheet.

11. The absorbent article of claim 10, wherein the first direction is away from the backsheet.

12. The absorbent article of claim 10, wherein the second direction is towards the backsheet.

13. The absorbent article of claim 10, wherein at least some of the cleft sidewalls directly contact the backsheet.

14. The absorbent article of claim 10, wherein the cleft sidewalls comprise some of the plurality of apertures.

15. The absorbent article of claim 10, wherein the topsheet further comprises a nonwoven that underlies the polymeric film, and wherein the nonwoven does not extend laterally to the same extent as the first and second wing portions.

16. The absorbent article of claim 10, wherein the main body portion of the topsheet comprises a plurality of film ruptures.

17. The absorbent article of claim 16, wherein the topsheet further comprises a nonwoven that underlies the polymeric film, and wherein fibers from the underlying nonwoven extend into and/or through at least some of the plurality of film ruptures.

18. An absorbent article, comprising:
a main body having a longitudinal centerline and a transverse centerline, the main body comprising an absorbent core;
first and second wings extending in directions parallel to the transverse centerline and outwardly from the main body on opposing sides of the longitudinal centerline; and
a topsheet comprising a first wing portion, a second wing portion, and a main body portion disposed between the first and second wing portions, wherein the topsheet comprises only a polymeric film and extending across the first wing and the second wing, and wherein the topsheet comprises both a polymeric film and nonwoven in the main body portion;
wherein the first and second wing portions of the topsheet comprise a plurality of clefts having cleft sidewalls that are buckled or tucked underneath the topsheet; and
wherein the main body portion of the topsheet comprises a plurality of polymeric film ruptures with fiber tufts originating from the nonwoven extending therethrough.

19. The absorbent article of claim 18, wherein the cleft sidewalls extend in a similar direction to that of the fibers tufts.

20. The absorbent article of claim 18, wherein the cleft sidewalls extend in a different direction to that of the fiber tufts.

* * * * *